United States Patent
Wang

(10) Patent No.: US 10,561,338 B2
(45) Date of Patent: Feb. 18, 2020

(54) ENDOSCOPE POSITION IDENTIFYING APPARATUS, ENDOSCOPE POSITION IDENTIFYING METHOD, AND RECORDING MEDIUM HAVING AN ENDOSCOPE POSITION IDENTIFYING PROGRAM RECORDED THEREIN

(71) Applicant: FUJIFILM Corporation, Tokyo (JP)

(72) Inventor: Caihua Wang, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 215 days.

(21) Appl. No.: 15/265,386

(22) Filed: Sep. 14, 2016

(65) Prior Publication Data
US 2017/0071504 A1     Mar. 16, 2017

(30) Foreign Application Priority Data

Sep. 16, 2015 (JP) .................. 2015-182839

(51) Int. Cl.
A61B 5/06      (2006.01)
A61B 1/00     (2006.01)
(Continued)

(52) U.S. Cl.
CPC ............ *A61B 5/066* (2013.01); *A61B 1/0005* (2013.01); *A61B 1/00009* (2013.01); *A61B 1/04* (2013.01);
(Continued)

(58) Field of Classification Search
CPC . A61B 1/00009; A61B 1/0005; A61B 1/2676; A61B 2034/101;
(Continued)

(56) References Cited

U.S. PATENT DOCUMENTS 7,641,609 B2 * 1/2010 Ohnishi ............. A61B 1/00009
                                                                  600/117
8,102,416 B2 * 1/2012 Ito ......................... A61B 34/20
                                                                  348/65
(Continued)

FOREIGN PATENT DOCUMENTS

JP    2010-220742 A    10/2010
JP    2012-505695 A     3/2012
(Continued)

OTHER PUBLICATIONS

Office Action dated Jan. 29, 2019 in Japanese Patent Application No. 2015-182839 (with English translation).

*Primary Examiner* — John P Leubecker
*Assistant Examiner* — Shankar Raj Ghimire
(74) *Attorney, Agent, or Firm* — Birch, Stewart, Kolasch & Birch, LLP

(57) ABSTRACT

An image obtaining unit obtains actual endoscope images, and a virtual endoscope image generating unit generates virtual endoscope images including a plurality of virtual endoscope branch images. A corresponding virtual endoscope image determining unit obtains a plurality of actual endoscope images which were obtained within a predetermined amount of time before the endoscope reached its current position, compares the plurality of actual endoscope images and the plurality of virtual endoscope branch images, and determines a corresponding virtual endoscope image that corresponds to the branch structure closest to the current position of the endoscope, through which the endoscope has passed. A matching unit performs matching between each of a plurality of actual endoscope path images and a plurality of virtual endoscope path images for each of a plurality of paths. A position identifying unit identifies the current (Continued)

position of a leading end of the endoscope based on the results of matching.

12 Claims, 9 Drawing Sheets

(51) Int. Cl.
*A61B 1/04* (2006.01)
*A61B 1/267* (2006.01)
*A61B 34/20* (2016.01)

(52) U.S. Cl.
CPC .... *A61B 1/2676* (2013.01); *A61B 2034/2057* (2016.02)

(58) Field of Classification Search
CPC .... A61B 2034/2057; A61B 2034/2065; A61B 2090/364; A61B 2090/365; A61B 2090/367; A61B 34/20; A61B 5/066; A61B 5/6847; A61B 5/7425; B25J 9/1671; B25J 9/1689
USPC ........................................................ 600/117
See application file for complete search history.

(56) References Cited

U.S. PATENT DOCUMENTS

| | | | | |
|---|---|---|---|---|
| 9,326,660 | B2* | 5/2016 | Akimoto | A61B 1/00009 |
| 9,830,737 | B2* | 11/2017 | Sakuragi | G06T 19/20 |
| 2009/0161927 | A1* | 6/2009 | Mori | A61B 6/466 382/128 |
| 2011/0184238 | A1* | 7/2011 | Higgins | A61B 1/00009 600/117 |
| 2011/0234780 | A1 | 9/2011 | Ito et al. | |
| 2011/0282151 | A1* | 11/2011 | Trovato | A61B 5/06 600/117 |
| 2012/0203065 | A1* | 8/2012 | Higgins | A61B 1/2676 600/109 |
| 2012/0203067 | A1* | 8/2012 | Higgins | A61B 1/00006 600/117 |
| 2012/0287238 | A1* | 11/2012 | Onishi | A61B 1/0005 348/45 |
| 2014/0180063 | A1* | 6/2014 | Zhao | G06T 7/75 600/424 |
| 2014/0336501 | A1* | 11/2014 | Masumoto | A61B 6/12 600/417 |

FOREIGN PATENT DOCUMENTS

| | | | | |
|---|---|---|---|---|
| JP | 2013-517909 A | | 5/2013 | |
| WO | WO-2004010857 A1 | * | 2/2004 | ......... A61B 1/00009 |
| WO | WO-2004023986 A1 | * | 3/2004 | ......... A61B 1/00009 |
| WO | WO 2011/102012 A1 | | 8/2011 | |
| WO | 2013-150650 A | | 8/2013 | |
| WO | WO-2013111535 A1 | * | 8/2013 | ............... A61B 6/12 |
| WO | WO-2014156378 A1 | * | 10/2014 | ......... A61B 1/00009 |

* cited by examiner

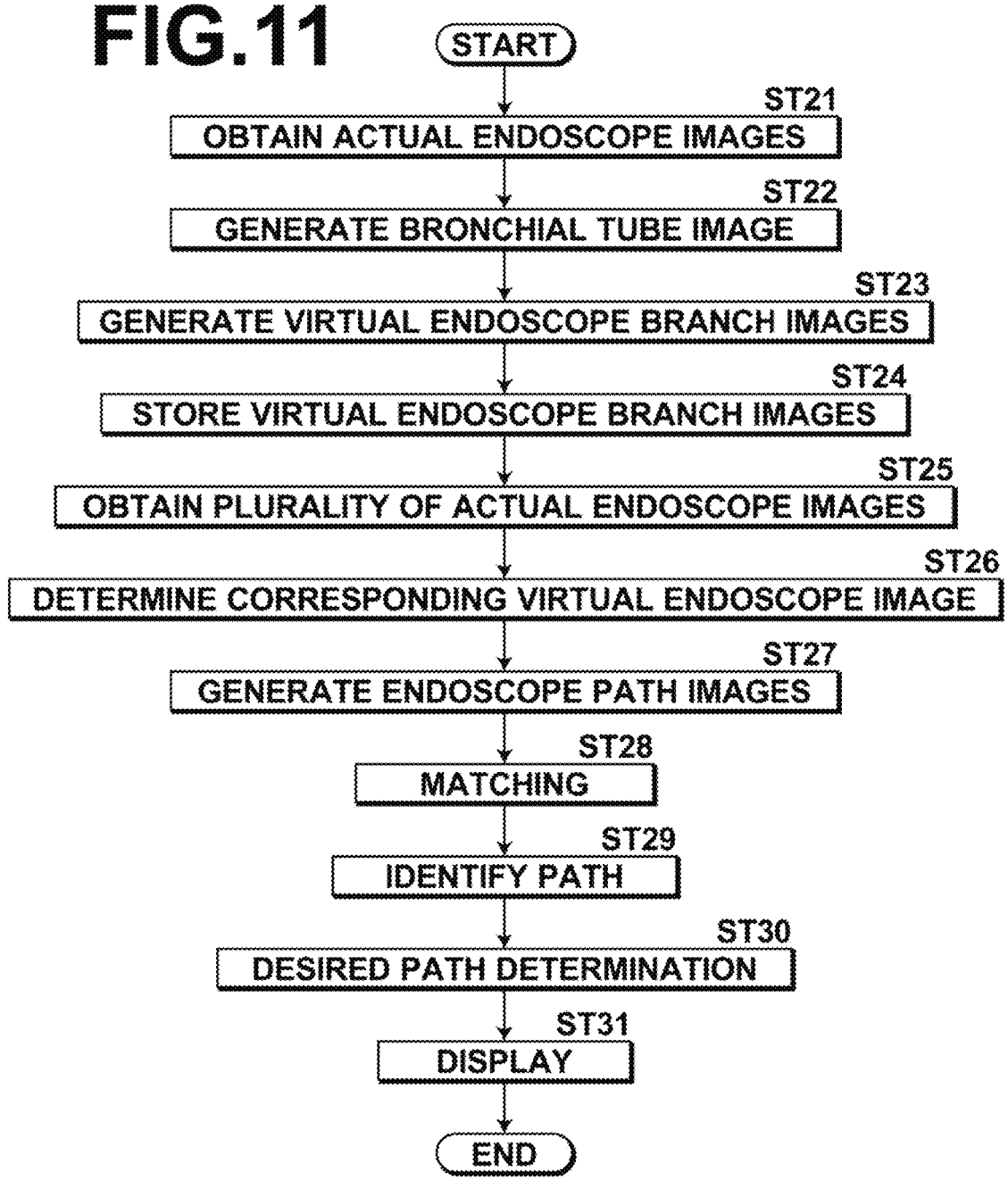

ENDOSCOPE POSITION IDENTIFYING APPARATUS, ENDOSCOPE POSITION IDENTIFYING METHOD, AND RECORDING MEDIUM HAVING AN ENDOSCOPE POSITION IDENTIFYING PROGRAM RECORDED THEREIN

CROSS REFERENCE TO RELATED APPLICATIONS

The present application claims priority under 35 U.S.C. § 119 to Japanese Patent Application No. 2015-182839 filed on Sep. 16, 2015. The above application is hereby expressly incorporated by reference, in its entirety, into the present application.

BACKGROUND

The present disclosure is related to an apparatus, a method, and a program for positioning an endoscope that identify the position of an endoscope within a lumen structure when the endoscope is inserted into a lumen structure having branching structures such as bronchial tubes to observe the lumen structure.

Recently, attention is being focused on techniques for observing or operating on lumen structures of patients, such as the large intestines and the bronchial tubes, using endoscopes. However, although endoscopes are capable of obtaining images in which the colors and textures of the interiors of lumen structures are clearly represented by use of imaging elements such as a CCD (Charge Coupled Device), these images are two dimensional representations of the interiors of the lumen structures. For this reason, it is difficult to understand what portion of the interior of the lumen structure is being represented by endoscope images. Particularly, because endoscopes for the bronchial tubes are thin and have narrow fields of view, it is difficult for the leading ends of such endoscopes to reach the target positions thereof.

Therefore, techniques for generating virtual endoscope images that approximate images which are actually obtained by an endoscope, employing three dimensional images obtained by tomographic imaging using a modality such as a CT (Computed Tomography) apparatus and an MRI (Magnetic Resonance Imaging) apparatus, are being proposed. The virtual endoscope images are employed as navigating images to guide an endoscope to a target position within a lumen structure. However, experience and technique are required to guide the leading end of an endoscope to a target position within a short period of time in the case that the lumen structure has paths that branch in multiple steps, such as the bronchial tubes.

For this reason, a method in which an image of a lumen structure is extracted from a three dimensional image, the image of the lumen structure and an actual endoscope image, which is actually obtained by performing imaging with an endoscope, are matched, and a virtual endoscope image for the current position of the endoscope is generated from the three dimensional image of the lumen structure, has been proposed (refer to Japanese Unexamined Patent Publication No. 2013-150650).

Meanwhile, it is important for an endoscope to be guided through a path that leads to a target position at branching positions within lumen structures, in order for the endoscope to reach the target position. For this reason, methods for identifying the current position of an endoscope by matching actual endoscope images of branching positions, which are obtained by the endoscope, and virtual endoscope images of branching positions, have been proposed (refer to PCT Japanese Publication No. 2013-517909, PCT Japanese Publication No. 2012-505695, and International Patent Publication No. WO2011/102012). According to the methods of PCT Japanese Publication No. 2013-517909, PCT Japanese Publication No. 2012-505695, and International Patent Publication No. WO2011/102012, the current position of an endoscope can be identified, and therefore the leading end of an endoscope can be easily guided to a target position.

SUMMARY

The branching positions within a virtual endoscope image can be identified by employing the methods of Japanese Unexamined Patent Publication No. 2013-150650, PCT Japanese Publication No. 2013-517909, PCT Publication No. 2012-505695, and International Patent Publication No. WO2011/102012. However, in the case that an endoscope passes through a branch and is positioned within a path between branches, an actual endoscope image only includes the inner walls of a lumen structure. That is, very few structural features are included in such an actual endoscope image. For this reason, it is extremely difficult to recognize which path from a previous branch an endoscope has been guided into in the case that the endoscope is guided beyond a branch position. In such a case, the endoscope may be retracted to the branch position, the path into which the endoscope is to be inserted can be reconfirmed, and the endoscope may be reinserted into the reconfirmed path. However, such operations pose great burdens both on an operator and on a patient. In addition, in the case that an endoscope is inserted into a path which is believed to be the correct path in error, the error in selecting the path will not be known until a next branch position appears. In such a case as well, it is necessary for the endoscope to be retracted to the previous branch position and reinserted into the correct path. Therefore, the efficiency in operations of inserting endoscopes is extremely poor.

The present disclosure has been developed in view of the foregoing circumstances. The present disclosure enables which lumen structure an endoscope is inserted into at branch positions to be identified.

An endoscope position identifying apparatus of the present disclosure comprises:

actual endoscope image obtaining means, for sequentially obtaining actual endoscope images that represent the inner walls of a lumen structure, generated by an endoscope which is inserted into a lumen structure having a plurality of branched structures within a subject;

virtual endoscope image generating means, for generating a plurality of virtual endoscope images that include a plurality of virtual endoscope branch images that represent the inner walls of the lumen structure for each of a plurality of viewpoint positions from which a plurality of branch structures are viewed, from a three dimensional image that includes the lumen structure of the subject;

corresponding virtual endoscope image determining means, for determining a corresponding virtual endoscope image that corresponds to a branch structure closest to the current position of the endoscope, through which the endoscope has passed;

matching means, for matching a plurality of virtual endoscope path images generated from a three dimensional image that represent each of a plurality of paths which are present at least in the direction of movement of the endoscope from a corresponding branch viewpoint position for which the corresponding virtual endoscope image was generated, for each of a plurality of viewpoint positions, and a plurality of actual endoscope path images obtained along a path from the branch structure through which the endoscope has passed to the current position of the endoscope, for each of a plurality of paths; and position identifying means, for identifying the current position of the endoscope from among the plurality of paths, based on the results of matching.

In the case that an endoscope is inserted into a lumen structure, only a single lumen structure is present prior to a branch structure. However, the lumen structure branches into a plurality of paths beyond the branch structure. For this reason, one path along which the endoscope can move is present prior to a branch position, and a plurality of paths along which the endoscope can move are present beyond the branch structure. The "plurality of paths which are present at least in the direction of movement of the endoscope from a corresponding branch viewpoint position" may be beyond the corresponding branch viewpoint position, that is, only the plurality of paths which are present in the direction of movement of the endoscope, or may be the plurality of paths that include the one path prior to the corresponding branch viewpoint position.

The "matching" operation refers to calculating index values that represent the degree to which the plurality of virtual endoscope path images and the plurality of actual endoscope path images match, for each of the plurality of paths. The index values are the results of matching. Note that the degree of similarity between the plurality of virtual endoscope path images and the plurality of actual endoscope path images may be employed as the index value.

Note that the endoscope position identifying apparatus of the present disclosure may further comprise identification result output means, for outputting the results of identification obtained by the position identifying means.

In addition, the endoscope position identifying apparatus of the present disclosure may further comprise determining means, for determining whether the endoscope is positioned along a desired path within the lumen structure based on the identification results obtained by the position identifying means.

In addition, in the endoscope position identifying apparatus of the present disclosure, the corresponding virtual endoscope image determining means may determine the corresponding virtual endoscope image, by comparing at least one actual endoscope branch image, obtained at the position of the closest branch structure through which the endoscope has passed, and a plurality of virtual endoscope branch images.

In addition, in the endoscope position identifying apparatus of the present disclosure, the corresponding virtual endoscope image determining means may determine the corresponding virtual endoscope image, by comparing a virtual endoscope branch image generated at a branch viewpoint position toward the side of direction of movement of the endoscope from a corresponding branch viewpoint position corresponding to a branch structure of the lumen structure through which the endoscope has passed, and at least one actual endoscope image.

In addition, the endoscope position identifying apparatus of the present disclosure may further comprise actual endoscope image identifying means, for identifying an actual endoscope branch image.

In addition, in the endoscope position identifying apparatus of the present disclosure, the actual endoscope image identifying means may perform processes for identifying an actual endoscope branch image at predetermined temporal intervals.

In addition, in the endoscope position identifying apparatus of the present disclosure, the virtual endoscope image generating means may generate the virtual endoscope path images after the corresponding virtual endoscope image is determined.

In addition, in the endoscope position identifying apparatus of the present disclosure, the virtual endoscope image generating means may generate virtual endoscope images including a plurality of virtual endoscope branch images and virtual endoscope path images which are set at predetermined intervals along the paths of a lumen structure within a three dimensional image; the endoscope position identifying apparatus may further comprise first storage means for storing virtual endoscope images for a plurality of viewpoint positions; and the matching means may obtain a plurality of virtual endoscope path images from the first storage means.

In addition, the endoscope position identifying apparatus of the present disclosure may further comprise second storage means for storing a plurality of actual endoscope images from the current position of the endoscope to the position of a branch structure through which the endoscope has passed.

An endoscope position identifying method of the present disclosure comprises:

sequentially obtaining actual endoscope images that represent the inner walls of a lumen structure, generated by an endoscope which is inserted into a lumen structure having a plurality of branched structures within a subject;

generating a plurality of virtual endoscope images that include a plurality of virtual endoscope branch images that represent the inner walls of the lumen structure for each of a plurality of viewpoint positions from which a plurality of branch structures are viewed, from a three dimensional image that includes the lumen structure of the subject;

determining a corresponding virtual endoscope image that corresponds to a branch structure closest to the current position of the endoscope, through which the endoscope has passed;

matching a plurality of virtual endoscope path images generated from a three dimensional image that represent each of a plurality of paths which are present at least in the direction of movement of the endoscope from a corresponding branch viewpoint position for which the corresponding virtual endoscope image was generated, for each of a plurality of viewpoint positions, and a plurality of actual endoscope path images obtained along a path from the branch structure through which the endoscope has passed to the current position of the endoscope, for each of a plurality of paths; and identifying the current position of the endoscope from among the plurality of paths, based on the results of matching.

Note that the endoscope position identifying method of the present disclosure may be provided as a program that causes a computer to execute the method.

According to the present disclosure, a corresponding virtual endoscope image that corresponds to a branch structure closest to the current position of the endoscope, through which the endoscope has passed, is determined. Then, matching of a plurality of virtual endoscope path images generated from a three dimensional image that represent each of a plurality of paths which are present at least in the direction of movement of the endoscope from a corresponding branch viewpoint position for which the corresponding virtual endoscope image was generated, for each of a plurality of viewpoint positions, and a plurality of actual endoscope path images obtained along a path from the branch structure through which the endoscope has passed to the current position of the endoscope, is performed for each of a plurality of paths. Further, the current position of the endoscope is identified from among the plurality of paths, based on the results of matching. Therefore, which path the endoscope is positioned in, in the movement direction of the endoscope from the branch structure closest to the current position of the endoscope, through which the endoscope has passed, can be identified. Accordingly, whether the endoscope is in a correct path or an incorrect path after passing through the branch structure can be easily recognized. As a result, diagnosis employing the endoscope can be performed accurately.

BRIEF DESCRIPTION OF THE DRAWINGS

FIG. 11 is a diagram that illustrates the processes which are performed by a third embodiment.

DETAILED DESCRIPTION OF THE PREFERRED EMBODIMENTS

Figure 1:
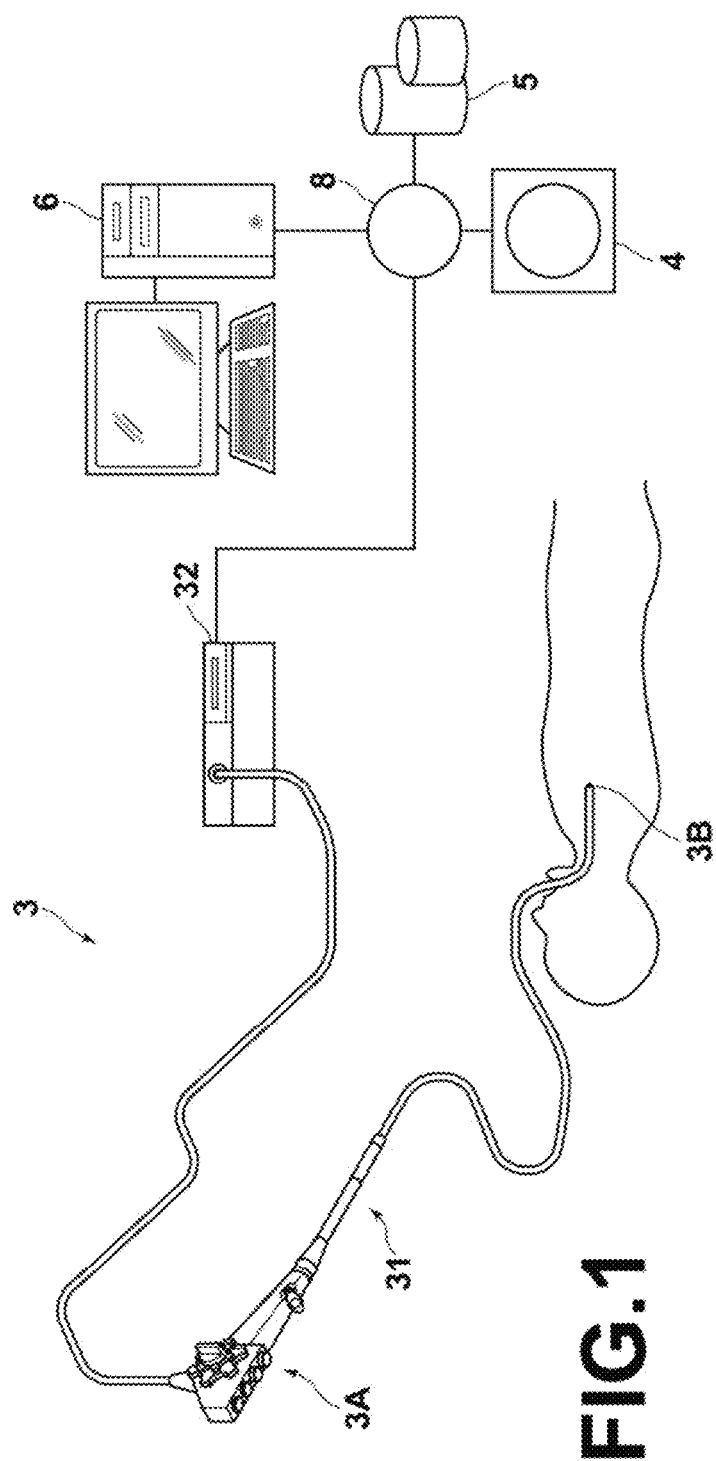
FIG. 1 is a schematic diagram that illustrates the hardware configuration of a diagnosis assisting system to which an endoscope position identifying apparatus according to an embodiment of the present disclosure is applied.

Hereinafter, embodiments of the present disclosure will be described with reference to the attached drawings. FIG. 1 is a schematic diagram that illustrates the hardware configuration of a diagnosis assisting system to which an endoscope position identifying apparatus according to an embodiment of the present disclosure is applied. In this system, an endoscope 3, a three dimensional image obtaining apparatus 4, an image storage server 6, and an endoscope position identifying apparatus 6 are connected via a network 8 so as to be capable of communicating with each other, as illustrated in FIG. 1.

The endoscope 3 is equipped with an endoscope scope 31 for imaging the interiors of lumen structures of subjects, and a processing device 32 for generating images of the interiors of lumen structures based on signals obtained by imaging.

The endoscope scope 31 is constituted by an insertion portion, which is to be inserted into lumen structures of subjects, mounted on an operating portion 3A. The endoscope scope 31 is connected to the processing device 32 via a universal cord which is detachably connected to the processing device 32. The operating portion 3A includes various buttons for issuing commands to bend the leading end 3B of the insertion portion within predetermined angular ranges in the vertical direction and the horizontal direction, to operate a piercing needle mounted on the leading end of the endoscope scope 31 to take tissue samples, and the like. In the present embodiment, the endoscope scope 31 is a flexible scope for use in bronchial tubes, and is inserted into the bronchial tubes of a subject. Light which is guided through an optical fiber from a light source device (not shown) provided in the processing device 32 is emitted from the leading end 3B of the insertion portion, and an imaging optical system of the endoscope scope 31 obtains images of the interior of the bronchial tubes of the subject. Note that the leading end 3B of the insertion portion of the endoscope scope 31 will hereinafter be referred to as "the leading end 3B of the endoscope", in order to simplify the description thereof.

The processing device 32 converts image signals obtained by the endoscope scope 31 into digital image signals, corrects image quality by digital signal processes such as white balance adjustment and shading correction, and generates endoscope images T0. Note that the generated images constitute a video formed by a plurality of endoscope images T0, which are obtained at a predetermined frame rate of 30 fps, for example. The endoscope images T0 are transmitted to the image storage server 5 or the endoscope position identifying apparatus 6. Hereinafter, the endoscope images T0 which are obtained by the endoscope will be referred to as "actual endoscope images T0", in order to distinguish them from virtual endoscope images to be described later.

The three dimensional image obtaining apparatus 4 images an examination target portion of the subject to generate a three dimensional image V0 that represents the examination target portion. Specifically, the three dimensional image obtaining apparatus 4 is a CT apparatus, an MRI apparatus, a PET (Positron Emission Tomography) apparatus, an ultrasound diagnostic apparatus, or the like. The three dimensional image V0 generated by the three dimensional image obtaining apparatus 4 is transmitted to the image storage server 5 and stored therein. In the present embodiment, the three dimensional image obtaining apparatus 4 generates a three dimensional image V0 that represents the thoracic portion which includes the bronchial tubes.

The image storage server 5 is a computer that stores and manages various types of data, and is equipped with a large capacity external memory device and database management software. The image storage server 5 communicates with the other components of the system via the network 8, to transmit image data and the like. Specifically, image data such as the actual endoscope images T0 obtained by the endoscope 3 and the three dimensional image V0 which is generated by the three dimensional image obtaining apparatus 2 are obtained via the network, then stored within a recording medium such as the large capacity external memory device and managed. Note that the actual endoscope images T0 are video data which are sequentially obtained accompanying movement of the leading end 3B of the endoscope. For this reason, it is preferable for the actual endoscope images T0 to be transmitted to the endoscope position identifying apparatus 6 without being processed through the image storage server 5. Note that the storage format of image data and communications among each component of the system via the network 8 are based on a protocol such as the DICOM (Digital Imaging and Communication in Medicine) protocol.

The endoscope position identifying apparatus 1 is a computer, in which an endoscope position identifying program according to an embodiment of the present disclosure is installed. The computer may be a work station or a personal computer which is directly operated by a physician who performs diagnosis, or may be a server computer connected to the work station or the personal computer via a network. The endoscope position identifying program is recorded on recording media such as a DVD (Digital Versatile Disc) and a CD-ROM (Compact Disc Read Only Memory) which are distributed, and installed onto the computer from the recording medium. Alternatively, the endoscope position identifying program is stored in a recording device of a server computer connected to a network or in a network storage, in a state accessible from the exterior, downloaded to the computer which is utilized by a physician who is the user of the endoscope position identifying apparatus 6 according to a request, then installed therein.

Figure 2:
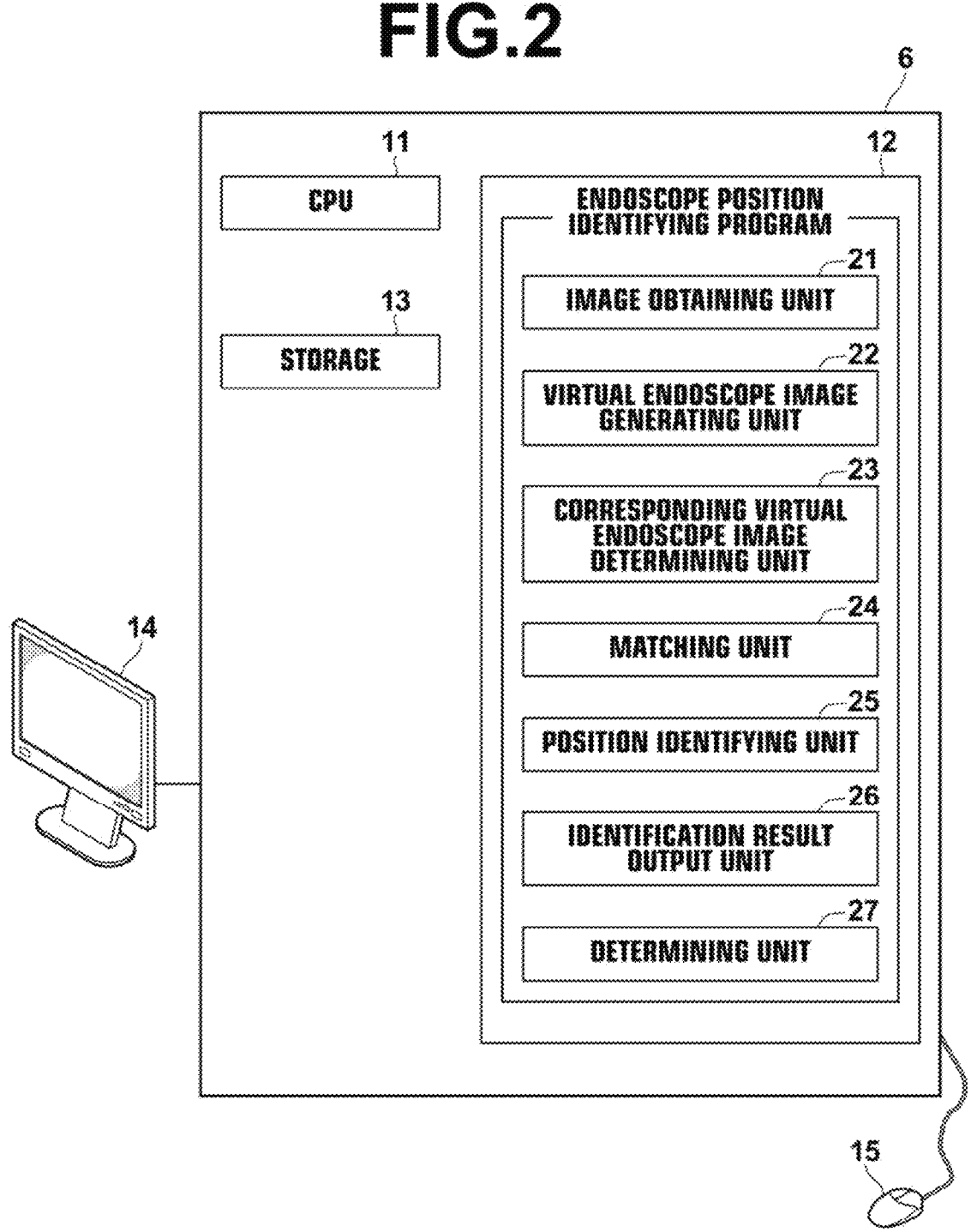
FIG. 2 is a schematic diagram that illustrates the configuration of an endoscope position identifying apparatus according to a first embodiment of the present disclosure, which is realized by installing a branch structure determining program in a computer.

FIG. 2 is a schematic diagram that illustrates the configuration of an endoscope position identifying apparatus, which is realized by installing an endoscope position identifying program in a computer. As illustrated in FIG. 2, the endoscope position identifying apparatus 6 is equipped with a CPU (Central Processing Unit) 11, a memory 12, and a storage 13, as components of a standard work station. In addition, a display 14 and an input section 15 such as a mouse are connected to the endoscope potion identifying apparatus 6.

The storage 13 has recorded therein images, such as the actual endoscope images T0 and the three dimensional image V0 which are obtained from the endoscope 3 and the three dimensional image obtaining apparatus 4 via the network 8, as well as images which are generated by processes performed by the endoscope position identifying apparatus 6.

In addition, the endoscope position identifying program is stored in the memory 12. The position aligning program defines an image obtaining process that sequentially obtains the actual endoscope images T0 generated by the processing device 32 as well as image data that represents the three dimensional image V0 generated by the three dimensional image obtaining apparatus 4; a virtual endoscope image generating process that generates virtual endoscope images including a plurality of virtual endoscope branch images that represent the inner walls of the bronchial tubes for each of a plurality of viewpoint positions from which a plurality of branch structures are viewed, from the three dimensional image V0; a corresponding virtual endoscope image determining process that determines a corresponding virtual endoscope image that corresponds to a branch structure closest to the current position of the endoscope, through which the endoscope has passed; a matching process that matches a plurality of virtual endoscope path images generated from the three dimensional image V0 that represent each of a plurality of paths which are present at least in the direction of movement of the endoscope from a corresponding branch viewpoint position for which the corresponding virtual endoscope image was generated, for each of a plurality of viewpoint positions, and a plurality of actual endoscope path images obtained along a path from the branch structure through which the endoscope has passed to the current position of the endoscope, for each of a plurality of paths; a position identifying process that identifies the current position of the endoscope from among the plurality of paths, based on the results of matching; an identification result output process that outputs the results of identification; and a determining process that determines whether the endoscope is positioned along a desired path within the bronchial tubes, as processes to be executed by the CPU 11.

The computer functions as an image obtaining unit 21, a virtual endoscope image generating unit 22, a corresponding virtual endoscope image determining unit 23, a matching unit 24, a position identifying unit 25, an identification result output unit 26, and a determining unit 27, by the CPU 11 executing the above processes according to the endoscope position identifying program. Note that the computer may be equipped with a plurality of processors that respectively perform each of the image obtaining process, the virtual endoscope image generating process, the corresponding virtual endoscope image determining process, the matching process, the position identifying process, the identification result output process, and the determining process. Here, the image obtaining unit 21 corresponds to an actual endoscope image obtaining means, and the storage 13 corresponds to a first and a second storage means.

The image obtaining unit 21 sequentially obtains actual endoscope images which are imaged by the endoscope 3 at predetermined viewpoint positions within the bronchial tubes, and also obtains the three dimensional image V0. In the case that the three dimensional image V0 is already recorded in the storage 13, the image obtaining unit 21 may obtain the three dimensional image V0 from the storage 13. The actual endoscope images T0 are displayed on the display 14. Note that the image obtaining unit 21 stores the obtained actual endoscope images T0 and the three dimensional image V0 in the storage 13.

The virtual endoscope image generating unit 22 generates virtual endoscope images K0 including a plurality of virtual endoscope branch images that represent the inner walls of the bronchial tubes for each of a plurality of viewpoint positions from which a plurality of branch structures are viewed, from the three dimensional image V0. The generation of the virtual endoscope images K0 will be described hereinafter.

First, the virtual endoscope image generating unit 22 extracts the bronchial tubes from the three dimensional image V0. Specifically, the virtual endoscope image generating unit 22 extracts a graph structure of a bronchial tube region included in an input three dimensional image V0 as a three dimensional bronchial tube image, employing the technique disclosed in Japanese Unexamined Patent Publication No. 2010-220742, for example. Hereinafter, an example of the method for extracting the graph structure will be described.

In the three dimensional image V0, pixels at the interiors of the bronchial tubes correspond to air regions, and are represented as regions having low pixel values. Meanwhile, the walls of the bronchial tubes are represented as cylindrical or linear structures having comparatively high pixel values. Therefore, structural analysis of shapes based on the distribution of pixel values is performed for each pixel, to extract the bronchial tubes.

Bronchial tubes branch at multiple steps, and the diameters of the bronchial tubes decrease at portions closer to the distal ends thereof. The virtual endoscope image generating unit 22 administers multiple resolution conversion on the three dimensional image V0 to generate a plurality of three dimensional images, in order to enable bronchial tubes of different sizes to be detected. A detection algorithm is applied to the three dimensional images of each of the resolutions, to detect lumen structures having different sizes.

First, Hessian matrices are calculated for each pixel of the three dimensional images of each resolution, and whether the pixel is that within a lumen structure is determined from the size relationship of eigenvalues of the Hessian matrices. The Hessian matrices are matrices having two step partial derivatives of density values in each axis (the x axis, the y axis, and the z axis of the three dimensional image). The Hessian matrices become 3×3 matrices when represented by Formula (1) below.

$$\nabla^2 I = \begin{bmatrix} I_{xx} & I_{xy} & I_{xz} \\ I_{xx} & I_{xy} & I_{xz} \\ I_{xx} & I_{xy} & I_{xz} \end{bmatrix} \quad (1)$$

$$I_{xx} = \frac{\delta^2 I}{\delta x^2}, I_{xy} = \frac{\delta^2 I}{\delta x \delta y^2}, \ldots$$

If the eigenvalues of a Hessian matrix of an arbitrary pixel are designated as $\lambda 1$, $\lambda 2$, and $\lambda 3$, it is known that the pixel is that which represents a lumen structure in the case that two of the eigenvalues are large while one of the eigenvalues is close to 0, for example, in the case that $\lambda 3, \lambda 2 \gg \lambda 1$ and $\lambda 1 \approx 0$ are satisfied. In addition, an eigenvector corresponding to the smallest eigenvalue ($\lambda 1 \approx 0$) of the Hessian matrix matches the direction of the principal axis of the lumen structure.

Bronchial tubes can be represented by a graph structure. However, lumen structures which are extracted in this manner may not necessarily be extracted as a single graph structure in which all of the lumen structures are connected, due to the influence of tumors or the like. Therefore, after detection of the lumen structures is completed within the entirety of the three dimensional image V0, whether the extracted lumen structures are within a predetermined distance and whether an angle formed between the direction of a baseline that connects arbitrary points within two extracted lumen structures and the direction of the principal axis of the lumen structure is within a predetermined angular range is evaluated. Whether a plurality of lumen structures are connected is determined based on the results of these evaluation, and the connective relationship among the extracted lumen structures is reconstructed. Extraction of the graph structure of the bronchial tubes is completed by this reconstruction.

The virtual endoscope image generating unit 22 classifies the extracted graph structure into a starting point, end points, branch points, and edges. A three dimensional graph structure that represents the bronchial tubes can be obtained as a bronchial tube image, by connecting the starting point, the end points, and the branch points with the edges. Here, the branch points are voxels having three or more links. Note that the method for generating the graph structure is not limited to that described above, and other methods may be applied.

Further, the virtual endoscope image generating unit 22 sets a plurality of viewpoint positions, which are set at predetermined intervals along paths along the graph structure of the bronchial tubes from the starting point to the end points thereof, as viewpoints. Note that the branch points are also set as viewpoints. Projected images, formed by projecting the three dimensional image V0 along sight lines that extend radially from the viewpoints in the direction of movement of the leading end 3B of the endoscope onto predetermined projection planes by the central projection method, are obtained as virtual endoscope images K0. Note that a known technique such as the volume rendering technique may be employed as the specific method for central projection. In addition, the angle of view (the range of the sight line) of each of the virtual endoscope images K0 and the center of the field of view (the center of the projection direction) are set in advance by input from a user.

The generated virtual endoscope images K0 are linked with each of the viewpoints along the graph structure of the bronchial tubes and stored in the storage 13. Particularly, the virtual endoscope images K0 which are generated with the branch points as the viewpoints thereof are designated as virtual endoscope branch images Kb. The virtual endoscope branch images Kb represent the inner walls of the bronchial tubes in the case that branching structures are viewed from the branch points. The virtual endoscope branch images Kb are linked with the branch points of the graph structure. In addition, the virtual endoscope images K0 generated for viewpoints along the edges of the graph structure are designated as virtual endoscope path images Kp, and linked with the viewpoints along the edges of the graph structures.

The corresponding virtual endoscope image determining unit 23 determines a corresponding virtual endoscope image Kbc that corresponds to the branch structure closest to the leading end 3B of the endoscope through which the leading end 3B of the endoscope has passed, from among a plurality of virtual endoscope branch images Kb. Specifically, at least one actual endoscope image T0 that includes an actual endoscope image at the position of the branch structure closest to the leading end 3B of the endoscope through which the leading end 3B of the endoscope has passed and a plurality of virtual endoscope branch images Kb are compared, to determine the corresponding virtual endoscope image Kbc.

Figure 3:
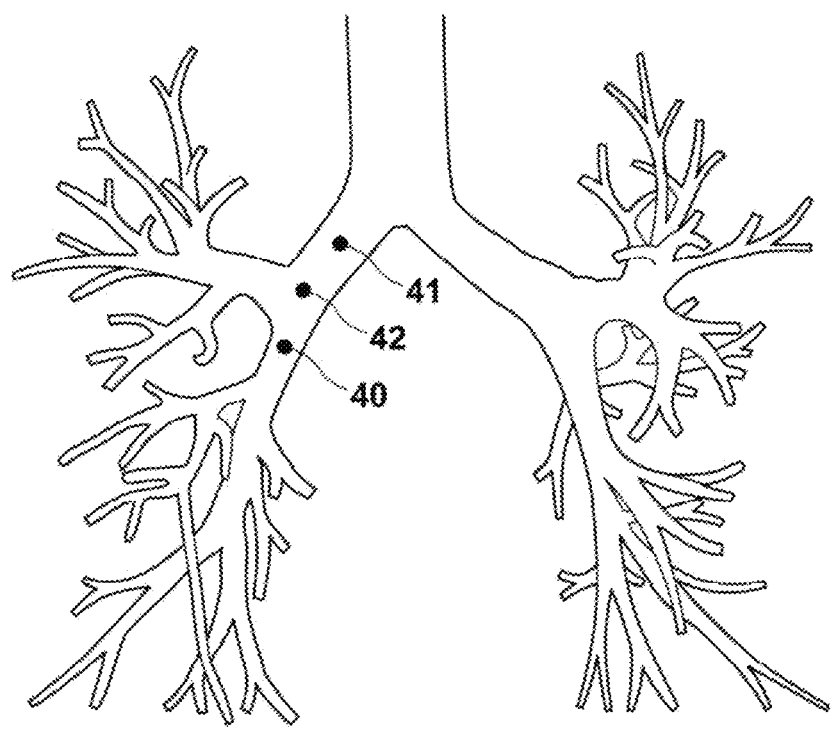
FIG. 3 is a diagram for explaining obtainment of a plurality of actual endoscope images.

For this reason, the corresponding virtual endoscope image determining unit 23 obtains a plurality of actual endoscope images Tni (i: 1~m, m is the number of images), which were obtained within a predetermined amount of time prior to the current point in time, from the storage 13. FIG. 3 is a diagram for explaining obtainment of a plurality of actual endoscope images. Here, the endoscope which has been inserted into the subject moves in the direction toward an end of the bronchial tubes as the direction of movement to a desired position. For this reason, the actual endoscope image of the branch structure will be included within the plurality of actual endoscope images T0 which were obtained within a predetermined amount of time prior to the current point in time. For example, assume a case in which the current position of the leading end 3B of the endoscope is point 40 within the bronchial tube image illustrated in FIG. 3, and the leading end 3B of the endoscope had been positioned at point 41 at a point in time which is a predetermined amount of time prior to the current point in time. A branch point 42 is included between the point 40 and the point 41. Therefore, an actual endoscope image obtained at the position of the branch structure will be included within the plurality of actual endoscope images Tni. Note that the predetermined amount of time may be one minute, for example, but the present disclosure is not limited to such a configuration. In addition, only one actual endoscope image may be obtained as the actual endoscope image obtained within the predetermined amount of time prior to the current point in time, as long as the actual endoscope image includes the branch structure. In the present embodiment, a plurality of actual endoscope images Tni are obtained.

The corresponding virtual endoscope image determining unit 23 compares the plurality of actual endoscope images Tni with the plurality of virtual endoscope branch images, and determines the corresponding virtual endoscope image Kbc that corresponds to the branch structure closest to the current position of the leading end 3B of the endoscope through which the leading end 3B of the endoscope has passed. Specifically, all of the correlative values between each of the plurality of actual endoscope images Tni and the plurality of virtual endoscope branch mages Kb are calculated. The actual endoscope image for which the greatest correlative value has been calculated is determined to be the actual endoscope branch image Tbc which was obtained at the position of the branch structure, and the virtual endoscope image Kb for which the greatest correlative value has been calculated is determined to be the corresponding virtual endoscope image. Note that the viewpoint position at the branch within the graph structure of the bronchial tubes at which the corresponding virtual endoscope image Kbc was generated is the corresponding branch viewpoint position.

Note that in the case that insertion of the endoscope has progressed and a corresponding virtual endoscope image Kbc has already been determined for a branch position that the leading end 3B of the endoscope has passed through already, only the virtual endoscope branch images Kb toward the direction of movement from the corresponding virtual endoscope image Kbc which has been determined already from among the plurality of virtual endoscope images Kb may be employed to determine a next corresponding virtual endoscope image Kbc. In addition, in the case that a path within the bronchial tubes along which the endoscope is to be inserted is determined, only the virtual endoscope images Kb which are linked with branch points along this path may be employed to determine the corresponding virtual endoscope image Kbc. By adopting these configurations, the amount of calculations required to determine the corresponding virtual endoscope image Kbc can be decreased, and the process can be performed expediently.

The matching unit 24 performs matching of a plurality of virtual endoscope path images Kp that represent each of a plurality of paths which are present in the direction of movement of the endoscope from a corresponding branch viewpoint position for which the corresponding virtual endoscope image Kbc was generated, for each of a plurality of viewpoint positions, and a plurality of actual endoscope path images obtained along a path from the branch structure through which the leading end 3B of the endoscope has passed to the current position of the endoscope, for each of a plurality of paths.

Figure 4:
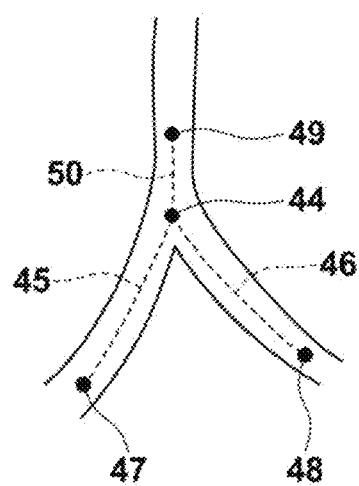
FIG. 4 is a diagram for explaining obtainment of a plurality of virtual endoscope path images.

FIG. 4 is a diagram for explaining obtainment of a plurality of virtual endoscope path images. Note that in FIG. 4 and FIG. 5 to be described later, the downward direction in the drawing sheet is the direction of movement of the endoscope. As illustrated in FIG. 4, if the position of the branch structure at which the corresponding virtual endoscope image Kbc was obtained, that is, the corresponding branch viewpoint position is designated as position 44, the bronchial tubes branch into two paths 45 and 46 in the direction of movement of the endoscope from the position 44. The matching unit 24 obtains a plurality of virtual endoscope path images Kp linked to a plurality of predetermined viewpoint positions from the corresponding branch viewpoint position 44 with respect to each of the paths 45 and 46 from the storage 13. Thereby, a plurality of virtual endoscope path images Kp1 from the corresponding branch viewpoint position 44 to a position 47, for example, are obtained for the path 45, and a plurality of virtual endoscope path images Kp2 from the corresponding branch viewpoint position 44 to a position 48, for example, are obtained for the path 46. Note that virtual endoscope path images Kp may be obtained for a path 50 to a position 49 opposite the direction of movement of the endoscope from the corresponding branch viewpoint position 44 in addition to the virtual endoscope path images Kp from the corresponding branch viewpoint position 44 and the paths 45 and 46.

Figure 5:
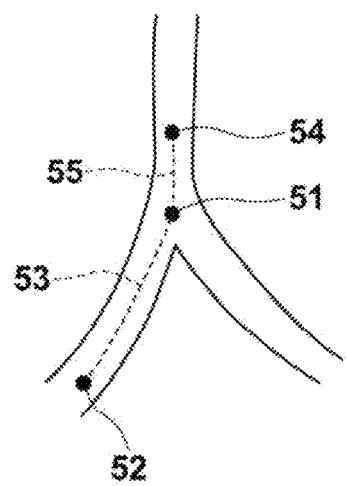
FIG. 5 is a diagram for explaining obtainment of a plurality of actual endoscope path images.

FIG. 5 is a diagram for explaining obtainment of a plurality of actual endoscope path images. As illustrated in FIG. 5, the position at which the actual endoscope branch image Tbc was obtained, that is the branch position, is designated as position 51. The matching unit 24 obtains a plurality of actual endoscope path images Tp along a path 53 from the branch position 51 to the current position 52 of the leading end 3B of the endoscope from the storage 13. Note that actual endoscope path images Tp may be obtained for a path 55 to a position 54 opposite the direction of movement of the endoscope from the branch position 51 in addition to the actual endoscope path images Tp from the branch position 51 and the path 53.

The matching unit 24 performs matching between each of the plurality of actual endoscope path images Tp and each of the plurality of virtual endoscope path images Kp1 as well as each of the plurality of virtual endoscope path images Kp2. The matching is performed by calculating the degree of similarity between each of the plurality of actual endoscope path images Tp and each of the plurality of virtual endoscope path images Kp1 as well as each of the plurality of virtual endoscope path images Kp2. Here, the degrees of similarity among the plurality of images are calculated by maximizing the correlative value of the plurality of virtual endoscope path images Kp1 and the plurality of virtual endoscope path images Kp2 using Formula (2) below. The technique that employs Formula (2) is a DP (Dynamic Programming) technique.

$$\operatorname*{argmax}_{j_k, k=1,\ldots k} \sum_{k=1}^{K} S(v_k, r_{j_k}) \quad (2)$$

subject to: $j_{k+1} > j_{k+1}$; for all $k$

In Formula (2), $v_k$ is a kth virtual endoscope image from among the virtual endoscope path images Kp, $r_{jk}$ is an actual endoscope image that corresponds to a virtual endoscope image vk from among the plurality of actual endoscope path images Tp, K is the number f virtual endoscope path images, and $S(v_k, r_{ik})$ is a function that calculates the correlative value between the virtual endoscope image $v_k$ and the actual endoscope image $r_{jk}$. Note that the number of virtual endoscope path images and the number of actual endoscope path images are different. Therefore, the virtual endoscope images within the virtual endoscope path images and the actual endoscope images within the actual endoscope path images Tk will not necessarily correspond to each other on a 1 to 1 basis. For this reason, n the present embodiment, Formula (2) is employed to calculate the correlative values among all of the virtual endoscope images included in the virtual endoscope path images and all of the actual endoscope images included in the actual endoscope path images, and calculates the sum of each row or the sum of the maximum value in each column in the case that the correlative values are arranged in a two dimensional matrix in the order that the actual endoscope path images Tp and the virtual endoscope images Kp are obtained, as the degree of similarity. Note that in the case that the virtual endoscope path images Kp are arranged in the horizontal direction and the actual endoscope path images Tp are arranged in the vertical direction within this matrix, Formula (2) is that which calculates the sums of the maximum values within each row.

The matching unit 24 calculates the degree of similarity for each of the virtual endoscope path images Kp employing Formula (2), and determines a virtual endoscope path image Kpmax, for which the degree of similarity is maximal. For example, in the case that the degree of similarity of an actual endoscope path images Tp to a virtual endoscope path image KP1 is greater than the degrees of similarity of the actual endoscope path images Tp to a virtual endoscope path image KP2, the matching unit 24 determines the virtual endoscope path image Kp1 to be the virtual endoscope path image Kpmax, for which the degree of similarity is maximal.

The position identifying unit 25 identifies the path, for which the virtual endoscope path image Kpmax having the maximal degree of similarity has been obtained, as the path of the current position of the leading end 3B of the endoscope.

The identification result output unit 26 outputs the results of identification, by displaying the identification results of the current position of the leading end 3B of the endoscope, which has been identified by the position identifying unit 25, on the display 14.

The determining unit 27 determines whether the leading end 3B of the endoscope is positioned along a desired path within the bronchial tubes, based on the identification results of the current position of the leading end 3B of the endoscope, which has been identified by the position identifying unit 25.

Figure 6:
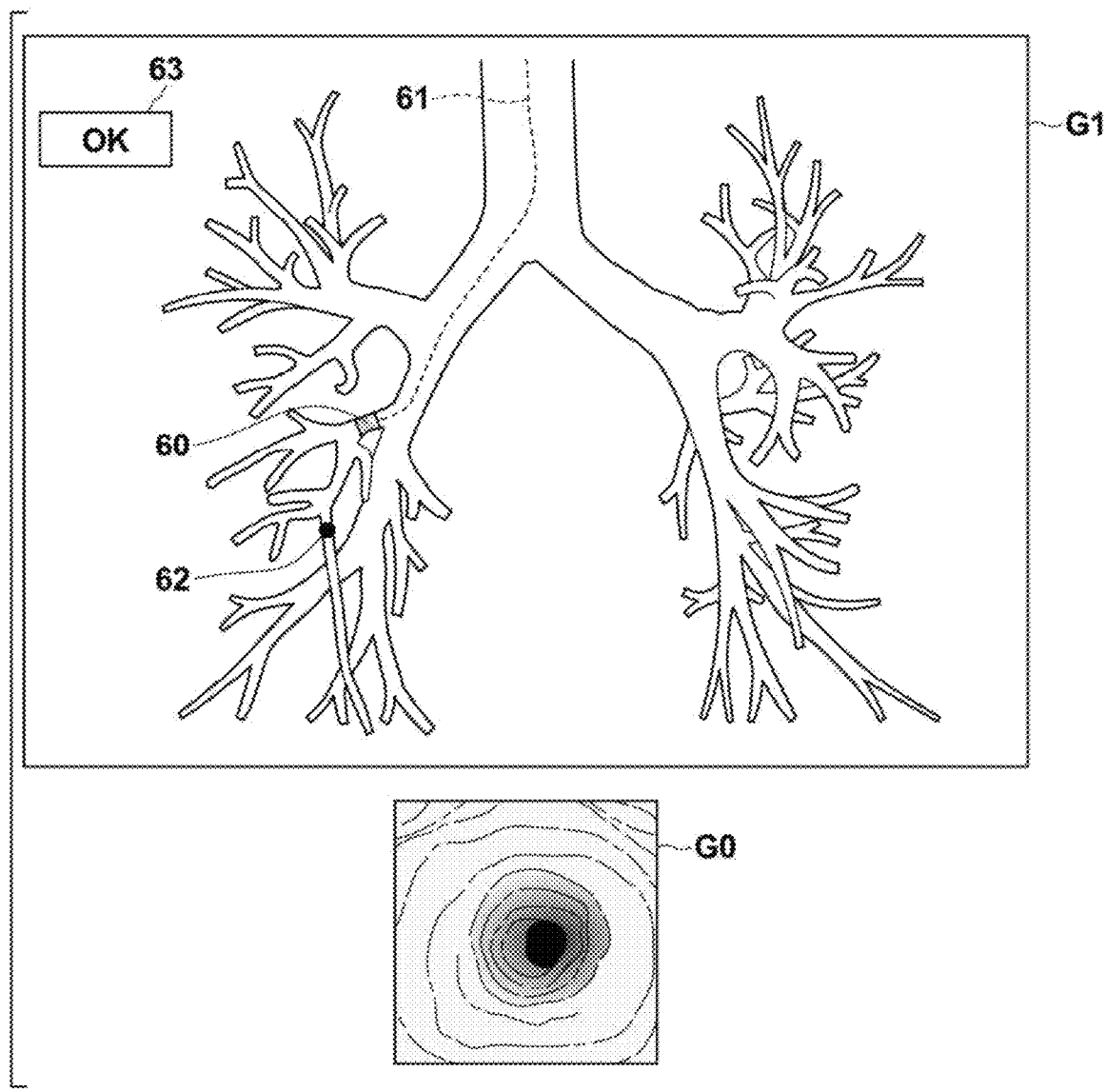
FIG. 6 is a diagram that illustrates identification results and determination results which are displayed on a display.

FIG. 6 is a diagram that illustrates identification results and determination results which are displayed on the display 14. As illustrated in FIG. 6, a current actual endoscope image G0 and a bronchial tube image G1 are displayed on the display 14. Within the bronchial tube image G1, the color of a path 60 in which the leading end 3B of the endoscope is currently positioned is displayed in a different color than other paths within the bronchial tubes. FIG. 6 illustrates the difference in display colors by hatching. Note that the path to the current position of the leading end 3B of the endoscope may be displayed by a broken line 61 as illustrated in FIG. 6. In addition, a target position 62 for the leading end 3B of the endoscope may also be displayed.

In FIG. 6, the target position 62 is present along the path 60 beyond the current position of the leading end 3B of the endoscope. Therefore, the determining unit 27 determines that the leading end 3B of the endoscope is positioned along a desired path that enables the leading end 3B of the endoscope to reach the target position 62. Accordingly, a determination result 63 indicating "OK" is displayed. In this case, the operator can cause the leading end 3B of the endoscope to progress further toward the target position 62.

Figure 7:
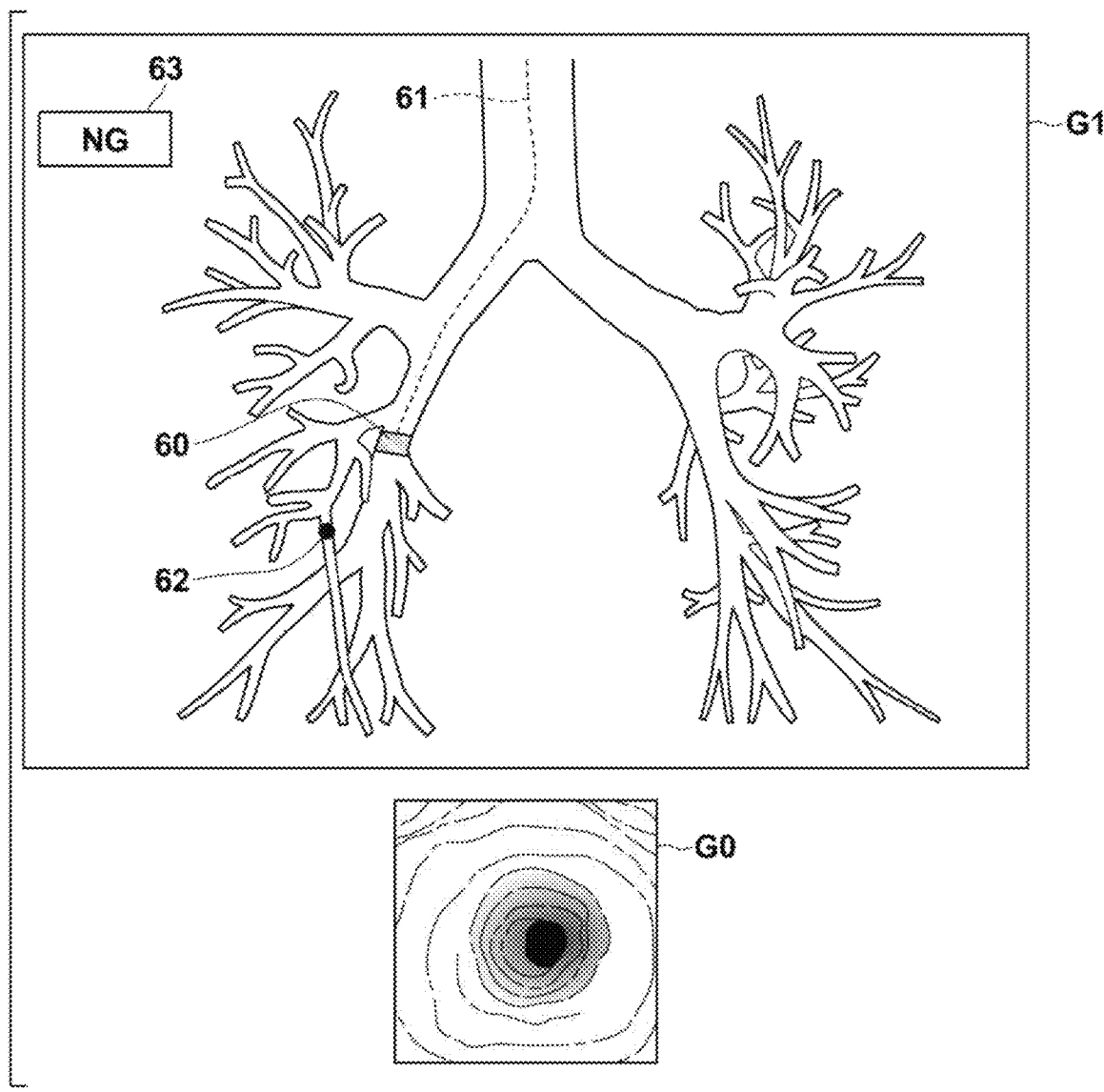
FIG. 7 is a diagram that illustrates identification results and determination results which are displayed on a display.

On the other hand, in the case that the target position 62 is not present along the path 60 beyond the current position of the leading end 3B of the endoscope as illustrated in FIG. 7, determining unit 27 determines that the leading end 3B of the endoscope is not positioned along a desired path that enables the leading end 3B of the endoscope to reach the target position 62. Accordingly, a determination result 63 indicating "NG (No Good)" is displayed. In this case, the operator can retract the endoscope to the closest branch position and insert the endoscope into the correct branch position, to cause the leading end 3B of the endoscope to progress along a desired path.

Note that the determination result 63 may be displayed only in cases that the leading end 3B of the endoscope is not positioned along a desired path. Conversely, the determination result 63 may be displayed only in cases that the leading end 3B of the endoscope is positioned along a desired path. In addition, the determination result may be output as an audio message or the like.

Figure 8:
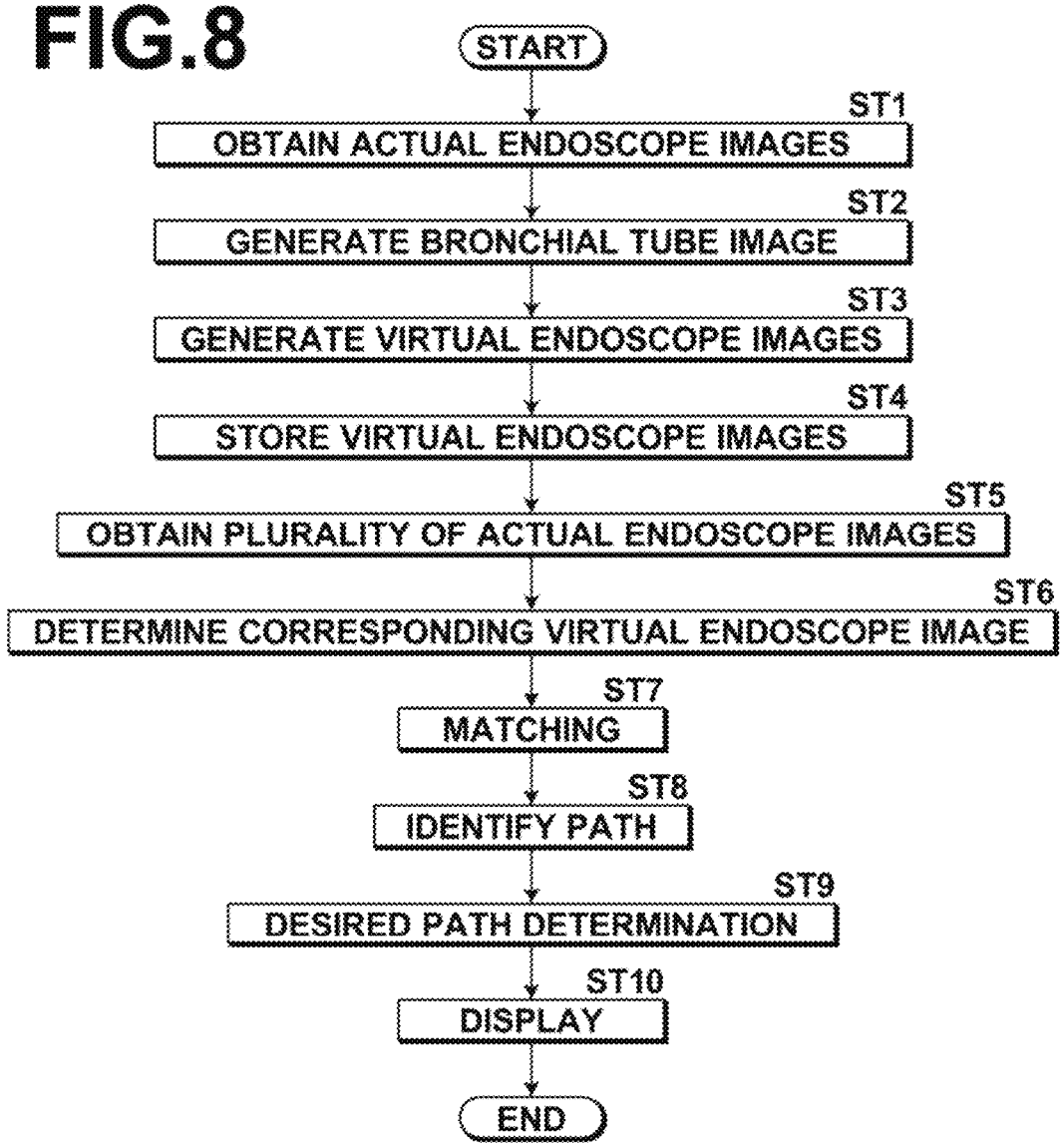
FIG. 8 is a flow chart that illustrates the processes which are performed by the first embodiment.

Next, the processes which are performed by the first embodiment will be described. FIG. 8 is a flow chart that illustrates the processes which are performed by the first embodiment. Note that here, it is assumed that a three dimensional image V0 has been obtained by the image obtaining unit 21 and is stored in the storage 13. First, the image obtaining unit 21 obtains actual endoscope images T0 (step ST1). The virtual endoscope image generating unit 22 generates a bronchial tube image from a three dimensional image V0 (step ST2), and further generates virtual endoscope images K0 that include a plurality of virtual endoscope branch images Kb (step ST3). The virtual endoscope image generating unit 22 links the virtual endoscope images K0 with viewpoints within the graph structure of bronchial tubes, and stores the linked virtual endoscope images K0 in the storage 13 (step ST4).

Next, the corresponding virtual endoscope image determining unit 23 obtains a plurality of actual endoscope images Tni, which were obtained within a predetermined amount of time prior to the current point in time, from the storage 13 (step ST5). Then, the corresponding virtual endoscope image determining unit 23 compares a plurality of actual endoscope images Tni and the plurality of virtual endoscope branch images Kb, and determines a corresponding virtual endoscope image Kbc that corresponds to the branch structure closest to the current position of the leading end 3B of the endoscope, through which the leading end 3B of the endoscope has passed (step ST6).

Then, the matching unit 24 performs matching among a plurality of actual endoscope path images Tp and a plurality of virtual endoscope path images Kp for each of a plurality paths (step ST7), the position identifying unit 25 identifies the path that the current position of the leading end 3B of the endoscope is located in (step ST8), and the determining unit 27 determines whether the leading end 3B of the endoscope is positioned along a desired path within the bronchial tubes (Desired Path Determination: step ST9). Further, the identification result and the determination result are displayed on the display 14 (step ST10), and the process ends.

As described above, according to the first embodiment, which path the leading end 3B of the endoscope is positioned along, among paths which are present in the direction of movement of the endoscope from the branch structure closest to the current position of the leading end 3B of the endoscope, through which the leading end 3B of the endoscope has passed, can be identified. Accordingly, whether the leading end 3B of the endoscope is positioned in an incorrect path or a correct path after passing through the branch structure can be easily recognized. As a result, diagnosis using the endoscope can be performed with high accuracy.

In addition, whether the leading end 3B of the endoscope is positioned along a desired path within the bronchial tubes is determined based on the position identification result. Therefore, whether the leading end 3B of the endoscope is within an incorrect path or a correct path after passing through a branch structure can be more easily recognized.

Figure 9:
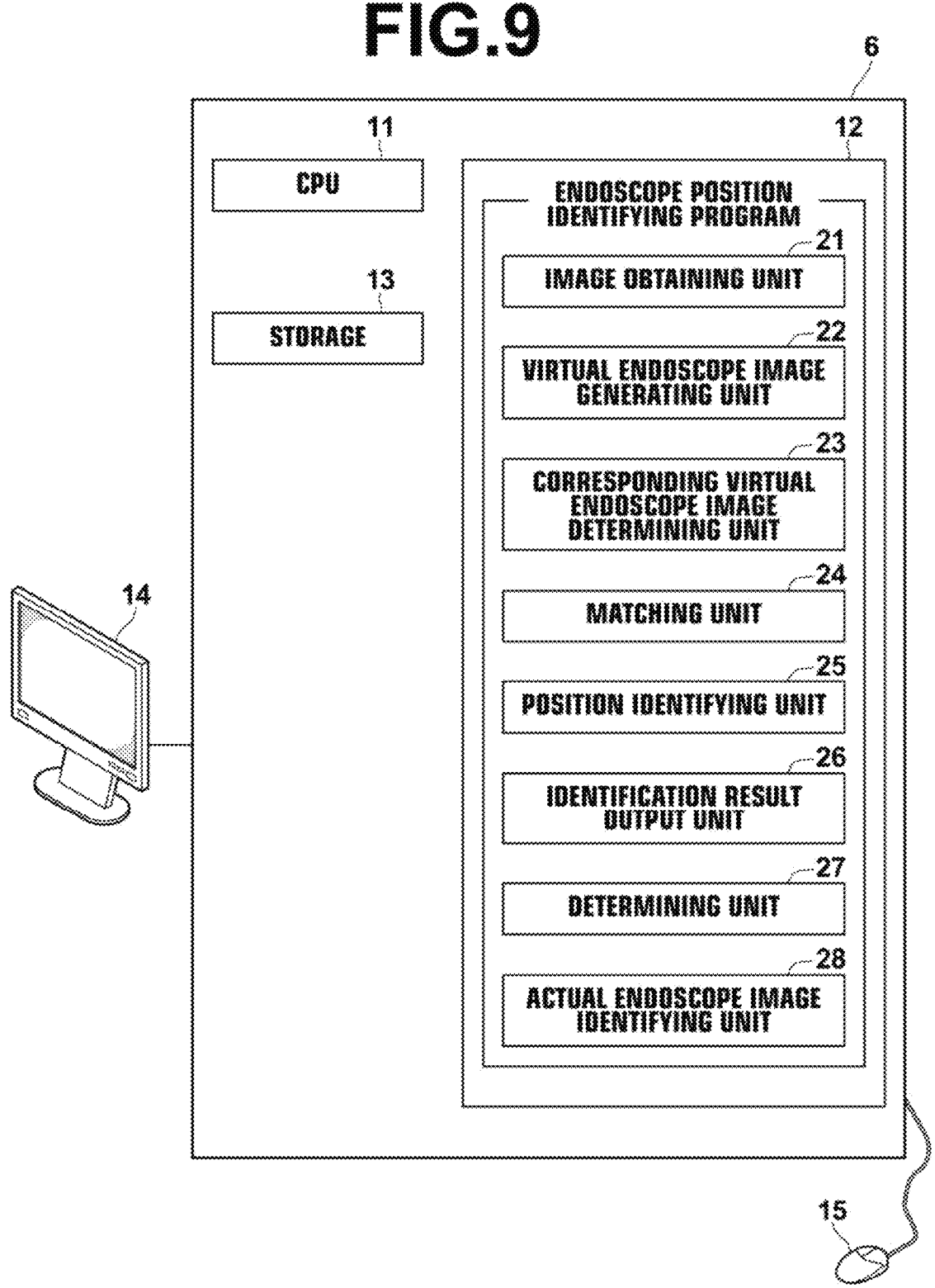
FIG. 9 is a schematic diagram that illustrates the configuration of an endoscope position identifying apparatus according to a second embodiment of the present disclosure, which is realized by installing a branch structure determining program in a computer.

Next, a second embodiment of the present disclosure will be described. FIG. 9 is a schematic diagram that illustrates the configuration of an endoscope position identifying apparatus according to the second embodiment. Configurations illustrated in FIG. 9 which are the same as those illustrated in FIG. 2 are denoted with the same reference numerals, and detailed descriptions thereof will be omitted. The second embodiment differs from the first embodiment in that the second embodiment is equipped with an actual endoscope image identifying unit 28 that identifies an actual endoscope branch image which was obtained at the position of a branch structure closest to the endoscope, through which the endoscope has passed.

The actual endoscope image identifying unit 28 continuously determines whether the actual endoscope images T0 which are sequentially obtained by image obtaining unit 21 include branch structures, and designates an actual endoscope image T0 that include branch structures as an actual endoscope branch image Tbc. Determination regarding whether branch structures are included may be performed by employing classifiers, for example. The classifiers are generated by machine learning that employs a plurality of actual endoscope images that include branch structures as learning data. Actual endoscope images are input to these classifiers, which output scores that represent the degree to which the actual endoscope images include branch structures. The actual endoscope image identifying unit 28 determines that an actual endoscope image includes a branch structure in the case that the score output from the classifiers exceed a predetermined threshold value, and designates such an actual endoscope image as an actual endoscope branch images Tbc.

Here, the matching unit 24 employs a plurality of actual endoscope path images Tp beyond the branch position, that is, actual endoscope path images Tp in the direction of movement of the leading end 3B of the endoscope from the branch position. By designating the actual endoscope branch image Tbc in advance as in the second embodiment, the matching process is possible using only actual endoscope images T0 at and beyond the latest actual endoscope branch image Tbc which are stored in the storage 13. Accordingly, by designating the actual endoscope branch image Tbc in advance and only storing actual endoscope images T0 at and beyond the latest actual endoscope branch image Tbc as in the second embodiment, the storage capacity for the actual endoscope images T0 within the storage 13 can be decreased.

Here, because paths of the bronchial tubes are present between branches in the bronchial tubes, a certain amount of time is required for the leading end 3B of the endoscope to pass through one branch and then to reach a next branch, when the leading end 3B of the endoscope is inserted into the bronchial tubes. For this reason, the processes for identifying the actual endoscope branch image Tbc may be performed at predetermined temporal intervals, every few seconds, for example. Thereby, the amount of calculations to be performed by the endoscope position identifying apparatus 6 can be reduced.

Note that designation of the actual endoscope branch image Tbc in the second embodiment is not limited to a technique that employs classifiers, and a template matching technique may be employed as an alternative. In this case, one or a plurality of images that include typical branch structures may be employed as templates, and correlative values may be calculated for the actual endoscope images T0 by performing template matching. An actual endoscope image T0 for which the correlative value exceeds a predetermined threshold may be designated as the actual endoscope branch image Tbc.

In addition, a plurality of virtual endoscope branch images Kb may be employed as templates when performing template matching. In this case, in the case that the actual endoscope branch image Tbc is determined as a result of performing template matching between the actual endoscope images T0 and all of the virtual endoscope branch images Kb, the corresponding virtual endoscope image determining unit 23 can immediately determine the virtual endoscope branch image Kb which had the highest correlative value as the corresponding virtual endoscope image Kbc. For this reason, the amount of calculations required for the processes to be performed by the corresponding virtual endoscope image determining unit 23 can be reduced.

Figure 10:
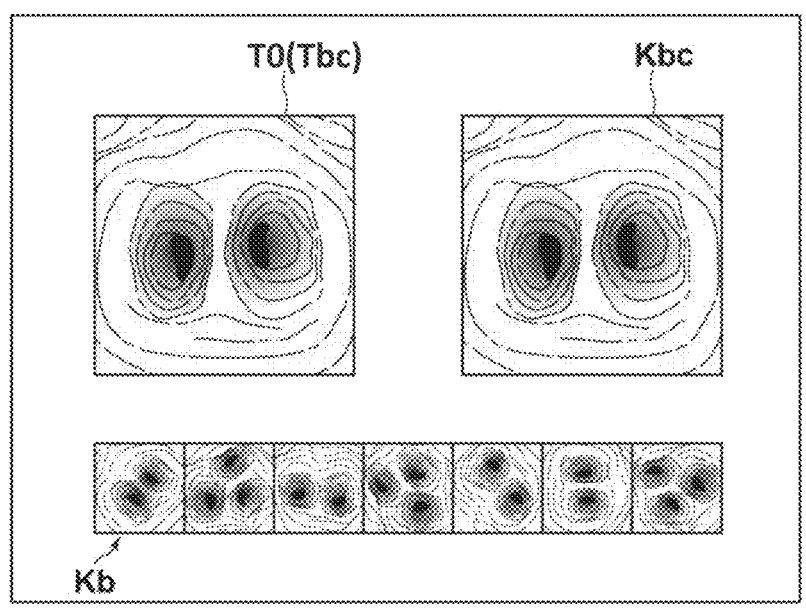
FIG. 10 is a diagram that illustrates an image that prompts an operator to select a corresponding virtual endoscope image, which is displayed on a display.

As a further alternative, the actual endoscope branch image Tbc may be designated by actual endoscope images T0 being displayed on the display 14, and by input of a result of determination regarding whether an actual endoscope image T0 is the actual endoscope branch image Tbc being received from an operator via the input section 15. In this case, a plurality of virtual endoscope branch images Kb may be displayed in addition to an actual endoscope image T0, as illustrated in FIG. 10. By adopting this configuration, the operator is enabled to compare the actual endoscope image T0 with the virtual endoscope branch images Kb, and to determine whether the displayed actual endoscope image T0 is the actual endoscope branch image Tbc. Further, by receiving selection of the corresponding virtual endoscope image Kbc that corresponds to te actual endoscope branch image Tbc, the corresponding virtual endoscope image Kbc can also be determined in addition fo the actual endoscope branch image Tbc.

Next, a third embodiment of the present disclosure will be described. Note that the configuration of the endoscope position identifying apparatus according to the third embodiment is the same as those of the endoscope position identifying apparatuses according to the first and second embodiments described above, and only the processes performed thereby differ. Therefore, detailed descriptions of the components of the apparatus will b omitted. In the first and second embodiments described above, the virtual endo scope path images Kp are generated by the virtual endoscope image generating unit 22 in advance. In the third embodiment, the virtual endoscope image generating unit 22 generates only the virtual endoscope branch images Kb in advance, and generates virtual endoscope path images Kp after a corresponding virtual endoscope image Kbc is determined. The virtual endoscope path images Kp are generated for each of a plurality of paths which are present in the direction of movement of the leading end 3B of the endoscope from the branch point to which the determined corresponding virtual endoscope image Kbc is linked.

FIG. 11 is a flow chart that illustrates the processes which are performed by the third embodiment. Note that here, it is assumed that a three dimensional image V0 has been obtained by the image obtaining unit 21 and is stored in the storage 13. First, the image obtaining unit 21 obtains actual endoscope images T0 (step ST21). The virtual endoscope image generating unit 22 generates a bronchial tube image from a three dimensional image V0 (step ST22), and further generates only a plurality of virtual endoscope branch images Kb from the three dimensional image V0 (step ST23). The virtual endoscope image generating unit 22 links the virtual endoscope branch images Kb with branch points within the graph structure of bronchial tubes, and stores the linked virtual endoscope branch images Kb in the storage 13 (step ST24).

Next, the corresponding virtual endo scope image determining unit 23 obtains a plurality of actual endoscope images Tni, which were obtained within a predetermined amount of time prior to the current point in time, from the storage 13 (step ST25). Then, the corresponding virtual endoscope image determining unit 23 compares a plurality of actual endoscope images Tni and the plurality of virtual endoscope branch images Kb, and determines a corresponding virtual endoscope image Kbc that corresponds to the branch structure closest to the current position of the leading end 3B of the endoscope, through which the leading end 3B of the endoscope has passed (step ST26).

Thereafter, the virtual endoscope image generating unit 22 generates virtual endoscope path images Kp for each of a plurality of paths which are present in the direction of movement of the leading end 3B of the endoscope from the branch point to which the determined corresponding virtual endoscope image Kbc is linked (step ST27).

Then, the matching unit 24 performs matching among a plurality of actual endoscope path images Tp and a plurality of virtual endoscope path images Kp for each of a plurality paths (step ST28), the position identifying unit 25 identifies the path that the current position of the leading end 3B of the endoscope is located in (step ST29), and the determining unit 27 determines whether the leading end 3B of the endoscope is positioned along a desired path within the bronchial tubes (Desired Path Determination: step ST30). Further, the identification result and the determination result are displayed on the display 14 (step ST31), and the process ends.

As described above, the virtual endoscope path images Kp are generated after the corresponding virtual endoscope image Kbc is determined in the third embodiment. Therefore, the volume of data of the virtual endoscope images K0 which are stored in the storage 13 can be degreased compared to the first and second embodiments. In addition, the amount of calculations to be performed by the virtual endoscope image generating unit 22 can be reduced, because it is not necessary to generate virtual endoscope path images Kp for all paths within the bronchial tubes.

Note that in the embodiments described above, the current position of the leading end 3B of the endoscope is identified when the endoscope is inserted toward a target position within the bronchial tubes from a branch position. The present disclosure may be applied to cases in which a plurality of target positions are present in the direction of movement of the leading end 3B of the endoscope from the branch position. Specifically, the present disclosure may be applied to a case in which a first target position at the end of a first path from a branch position is observed, the leading end 3B of the endoscope returns to the branch position, and then a second target position at the end of a second path different from the first path is observed. In this case, the determining unit 27 may designate the second path as the desired path and determine whether the leading end 3B of the endoscope is positioned along the desired path, in order to guide the leading end 3B of the endoscope to the second target position after the first target position is observed.

In addition, in the embodiments described above, the bronchial tube image is extracted from the three dimensional image V0, and the virtual endoscope images K0 are generated employing the bronchial tube image. Alternatively, the virtual endoscope images K0 may be generated from the three dimensional image V0 without extracting the bronchial tube image.

In addition, in the embodiments described above, the current position of the leading end 3B of the endoscope is identified when the endoscope is actually inserted into a subject. Alternatively, the actual endoscope images T0 may be saved, and the saved actual endoscope images T0 may be employed to investigate whether insertion of the endoscope was performed correctly, or utilized in education regarding insertion of endoscopes.

In addition, in the embodiments described above, cases in which the endoscope position identifying apparatus of the present disclosure was applied to observation of bronchial tubes were described. However, the present disclosure is not limited to such an application, and may be applied to cases in which lumen structures having branch structures, such as blood vessels, are to be observed with an endoscope as well.

The operative effects of the embodiments of the present disclosure will be described.

Whether an endoscope is positioned along a desired path within a lumen structure is determined based on the position identification result. Therefore, whether the endoscope is within an incorrect path or a correct path after passing through a branch structure can be more easily recognized.

In addition, a corresponding virtual endoscope image is determined by comparing a virtual endoscope branch image generated at a branch viewpoint position toward the side of direction of movement of the endoscope from a corresponding branch viewpoint position corresponding to a branch structure of the lumen structure through which the endoscope has passed, and at least one actual endoscope image. Thereby, the amount of calculations required to determine the corresponding virtual endoscope image can be reduced.

What is claimed is:

1. An endoscope position identifying apparatus, comprising:
    a processor configured to:
    sequentially obtain actual endoscope images that represent the inner walls of a lumen structure, generated by an endoscope which is inserted into the lumen structure having a plurality of branched structures within a subject by imaging the surface of the inner walls of the lumen structure by the endoscope;
    generate a plurality of virtual endoscope images that represent the surface of the inner walls of the lumen structure from a three dimensional image that includes the lumen structure of the subject, the plurality of virtual endoscope images including a plurality of virtual endoscope branch images that represent the branched structures at the surface of the inner walls of the lumen structure for each of a plurality of viewpoint positions from which the plurality of branched structures are viewed;
    determine a corresponding virtual endoscope image that corresponds to a branched structure of the surface of the inner walls of the lumen structure closest to a current position of the endoscope, through which the endoscope has passed, from the plurality of virtual endoscope branch images;
    match a plurality of virtual endoscope path images generated from the three dimensional image, the plurality of virtual endoscope path images representing the surface of the inner walls of the lumen structure of each of a plurality of paths which are present at least in a direction of movement of the endoscope from a corresponding branch viewpoint position for which the corresponding virtual endoscope image was generated, for each of a plurality of viewpoint positions, and a plurality of actual endoscope path images that represent the inner walls of the lumen structure and that are obtained along a path from the branched structure through which the endoscope has passed to the current position of the endoscope by imaging the surface of the inner walls of the lumen structure by the endoscope, for each of a plurality of paths; and
identify a path of the current position of the endoscope from among the plurality of paths, based on results of matching, wherein the path of the current position of the endoscope is a path where a virtual endoscope path image having a maximum degree of the matching with the plurality of actual endoscope path images is obtained.

2. An endoscope position identifying apparatus as defined in claim 1, wherein the processor is further configured to output the results of identification obtained by the processor.

3. An endoscope position identifying apparatus as defined in claim 1, wherein the processor is further configured to determine whether the endoscope is positioned along a desired path within the lumen structure based on the identification results obtained by the processor.

4. An endoscope position identifying apparatus as defined in claim 1, wherein:
the processor determines the corresponding virtual endoscope image, by comparing at least one actual endoscope branch image, obtained at the position of the closest branch structure through which the endoscope has passed, and a plurality of virtual endoscope branch images.

5. An endoscope position identifying apparatus as defined in claim 4, wherein:
the processor determines the corresponding virtual endoscope image, by comparing a virtual endoscope branch image generated at a branch viewpoint position toward the side of direction of movement of the endoscope from a corresponding branch viewpoint position corresponding to a branch structure of the lumen structure through which the endoscope has passed, and the at least one actual endoscope image.

6. An endoscope position identifying apparatus as defined in claim 4, wherein the processor is further configured to identify an actual endoscope branch image.

7. An endoscope position identifying apparatus as defined in claim 6, wherein:
the processor performs processes for identifying the actual endoscope branch image at predetermined temporal intervals.

8. An endoscope position identifying apparatus as defined in claim 1, wherein:
the processor generates the virtual endoscope path images after the corresponding virtual endoscope image is determined.

9. An endoscope position identifying apparatus as defined in claim 1, wherein:
the processor generates virtual endoscope images including the plurality of virtual endoscope branch images and the virtual endoscope path images which are set at predetermined intervals along the paths of a lumen structure within a three dimensional image;
the endoscope position identifying apparatus further comprises a first storage for storing virtual endoscope images for a plurality of viewpoint positions; and
the processor obtains the plurality of virtual endoscope path images from the first storage.

10. An endoscope position identifying apparatus as defined in claim 1, further comprising:
a second storage for storing a plurality of actual endoscope images from the current position of the endoscope to the position of the branch structure through which the endoscope has passed.

11. An endoscope position identifying method, comprising:
sequentially obtaining actual endoscope images that represent the inner walls of a lumen structure, generated by an endoscope which is inserted into a lumen structure having a plurality of branched structures within a subject by imaging the surface of the inner walls of the lumen structure by the endoscope;
generating a plurality of virtual endoscope images that represent the surface of the inner walls of the lumen structure from a three dimensional image that includes the lumen structure of the subject, the plurality of virtual endoscope images including a plurality of virtual endoscope branch images that represent the branched structures at the surface of the inner walls of the lumen structure for each of a plurality of viewpoint positions from which the plurality of branched structures are viewed;
determining a corresponding virtual endoscope image that corresponds to a branched structure of the surface of the inner walls of the lumen structure closest to the current position of the endoscope, through which the endoscope has passed, from the plurality of virtual endoscope branch images;
matching a plurality of virtual endoscope path images generated from a three dimensional image, the plurality of virtual endoscope path images representing the surface of the inner walls of the lumen structure of each of a plurality of paths which are present at least in the direction of movement of the endoscope from a corresponding branch viewpoint position for which the corresponding virtual endoscope image was generated, for each of a plurality of viewpoint positions, and a plurality of actual endoscope path images that represent the inner walls of the lumen structure and that are obtained along a path from the branched structure through which the endoscope has passed to the current position of the endoscope by imaging the surface of the inner walls of the lumen structure by the endoscope, for each of a plurality of paths; and
identifying a path of the current position of the endoscope from among the plurality of paths, based on the results of matching, wherein the path of the current position of the endoscope is a path where a virtual endoscope path image having a maximum degree of the matching with the plurality of actual endoscope path images is obtained.

12. A non transitory recording medium having an endoscope position identifying program recorded therein, the program causing a computer to execute the procedures of:
sequentially obtaining actual endoscope images that represent the inner walls of a lumen structure, generated by an endoscope which is inserted into a lumen structure having a plurality of branched structures within a subject by imaging the surface of the inner walls of the lumen structure by the endoscope;
generating a plurality of virtual endoscope images that represent the surface of the inner walls of the lumen structure from a three dimensional image that includes the lumen structure of the subject, the plurality of virtual endoscope images including a plurality of virtual endoscope branch images that represent the branched structures at the surface of the inner walls of the lumen structure for each of a plurality of viewpoint positions from which the plurality of branched structures are viewed;

determining a corresponding virtual endoscope image that corresponds to a branched structure of the surface of the inner walls of the lumen structure closest to the current position of the endoscope, through which the endoscope has passed, from the plurality of virtual endoscope branch images;

matching a plurality of virtual endoscope path images generated from a three dimensional image, the plurality of virtual endoscope path images representing the surface of the inner walls of the lumen structure of each of a plurality of paths which are present at least in the direction of movement of the endoscope from a corresponding branch viewpoint position for which the corresponding virtual endoscope image was generated, for each of a plurality of viewpoint positions, and a plurality of actual endoscope path images that represent the inner walls of the lumen structure and that are obtained along a path from the branched structure through which the endoscope has passed to the current position of the endoscope by imaging the surface of the inner walls of the lumen structure by the endoscope, for each of a plurality of paths; and identifying a path of the current position of the endoscope from among the plurality of paths, based on the results of matching, wherein the path of the current position of the endoscope is a path where a virtual endoscope path image having a maximum degree of the matching with the plurality of actual endoscope path images is obtained.

\* \* \* \* \*